United States Patent [19]

Fuisz

[11] Patent Number: 4,873,085

[45] Date of Patent: * Oct. 10, 1989

[54] SPUN FIBROUS COSMETIC AND METHOD OF USE

[75] Inventor: Richard C. Fuisz, Bethlehem, Pa.

[73] Assignee: Fuisz Pharmaceutical Ltd., Washington, D.C.

[*] Notice: The portion of the term of this patent subsequent to Aug. 8, 2006 has been disclaimed.

[21] Appl. No.: 169,914

[22] Filed: Mar. 18, 1988

Related U.S. Application Data

[63] Continuation-in-part of Ser. No. 40,371, Apr. 20, 1987, abandoned.

[51] Int. Cl.$^4$ .................... A61K 7/44; A61L 23/00; A23G 3/02
[52] U.S. Cl. .................... 424/400; 424/401; 424/439; 424/440; 424/443; 424/59; 424/60; 424/70; 514/777; 514/781; 426/658; 426/660; 426/517
[58] Field of Search .................... 514/772, 777, 781; 424/59, 60, 70, 400, 401, 431, 440, 443; 425/9; 426/658, 660, 517

[56] References Cited

U.S. PATENT DOCUMENTS

| | | | |
|---|---|---|---|
| 2,826,169 | 3/1958 | Le Veen | 424/59 |
| 3,019,745 | 2/1962 | Du Bois et al. | 425/9 |
| 3,036,532 | 5/1962 | Bowe | 425/9 |
| 3,070,045 | 12/1962 | Bowe | 425/9 |
| 3,073,262 | 1/1963 | Bowe | 425/9 |
| 3,324,061 | 6/1967 | Tanguery et al. | 264/177.13 |
| 3,557,717 | 1/1971 | Chivers | 426/517 |
| 3,595,675 | 7/1971 | Ash et al. | 426/658 |
| 3,615,671 | 10/1971 | Groesbeck et al. | 426/660 |
| 3,723,134 | 3/1973 | Chivers | 426/660 |
| 3,856,443 | 12/1974 | Salvi | 425/9 |
| 3,875,300 | 4/1975 | Homm et al. | 424/28 |
| 3,930,043 | 12/1975 | Warning et al. | 426/517 |
| 3,967,623 | 7/1976 | Butterworth et al. | 604/390 |
| 4,136,145 | 1/1979 | Fuchs et al. | 424/443 |
| 4,492,685 | 1/1985 | Keith et al. | 424/443 |
| 4,496,592 | 1/1985 | Kuwahara et al. | 426/5 |
| 4,526,525 | 7/1985 | Oiso et al. | 425/9 |
| 4,585,797 | 4/1986 | Cioca | 424/20 |

*Primary Examiner*—John Kight
*Assistant Examiner*—Nathan M. Nutter
*Attorney, Agent, or Firm*—Brooks Haidt Haffner & Delahunty

[57] ABSTRACT

A melt spinnable carrier agent such as sugar is combined with a cosmetic then converted into fiber form by melt spinning with "cotton candy" fabricating equipment. The as-spun product is converted to compacted individual dosage units. Examples are presented for topical application. All applications utilize the extraordinarily rapid entry of the fiber form mass into solution upon contact with a solvent. When lactose is used it absorbs moisture from the air which is then either transferred to the hair or skin to maintain the moisture content of the latter or it prevents the hair or skin from drying out.

25 Claims, No Drawings

SPUN FIBROUS COSMETIC AND METHOD OF USE

BACKGROUND OF THE INVENTION

This application is a continuation-in-part of application Ser. No. 040,371, filed Apr. 20, 1987 and now abandoned.

The present invention relates to a cosmetic product and to its method of use. More particularly, it relates to a dry form of a cosmetic that is rapidly dissoluble for use in topical treatment of hair or skin.

In the cosmetic field there are a considerable number of products for application to hair for conditioning, some with the object of softening the hair, some with the object of thickening the hair, some with the object of coloring, and even some with the alleged capability of inducing hair growth, and various combinations thereof. Similarly, there are many products for skin application, for softening, toning, coloring, for screening against sun burning, and the like. However, all such products as furnished to the user are either in the form of a liquid, a cream, or a salve or paste. As far as we are aware, non of the foregoing products is furnished in a completely dry state for either in situ entry into an aqueous solution or mixing with water immediately prior to application.

In my co-pending application mentioned above, there is described and claimed a rapidly dissoluble medicinal dosage unit in which a medicament is distributed on or incorporated in a fibrous mass of spun sugar fibers. The product is characterized by extremely rapid entry into solution when contacted with water or other liquid solvent. As explained in said application, the fibers, spun with a cotton candy spinning machine, are compacted without destroying the fibrous nature of the mass. The dosage unit can then be administered orally, dissolving almost instantaneously in the mouth.

It has now been discovered that the fiber form of product is ideally suited as a vehicle for carrying a cosmetic material and has other cosmetological attributes.

SUMMARY OF THE PRESENT INVENTION

In accordance with one aspect of the present invention there is provided a spun fibrous cosmetic composition comprising a rapidly dissoluble mass of water soluble spun fibers of a material capable of being spun into fibers that are readily water-soluble, and an effective quantity of an active agent distributed on or incorporated in said fibrous mass where said active agent has cosmetologic activity.

In accordance with another aspect of the present invention there is provided a spun fibrous cosmetic preparation comprising a rapidly dissoluble mass of water soluble spun fibers of lactose.

A further aspect of the present invention involves a method for treating hair or skin cosmetically which comprises applying to hair or skin a spun fibrous cosmetic preparation comprising a rapidly dissoluble mass of water soluble spun fibers of lactose.

Yet in accordance with a still further aspect of the present invention there is provided a method for treating hair or skin cosmetically which comprises applying to hair or skin a spun fibrous cosmetic composition comprising a rapidly dissoluble mass of water soluble spun fibers of a material capable of being spun into fibers that are readily water-soluble, and an effective quantity of an active agent distributed on or incorporated in said fibrous mass where at least said active agent has cosmetologic activity.

The invention will be better understood after reading the following detailed description of the presently preferred embodiments thereof.

DETAILED DESCRIPTION OF THE PRESENTLY PREFERRED EMBODIMENTS

The spun sucrose sugar fiber confection, commonly referred to as cotton candy, is well known to children and most adults. Also, it should be obvious to all who have eaten cotton candy that the sucrose sugar literally melts in the mouth and seems very quickly to disappear to nothing. In its spun form the sugar is very fragile. However, the sugar fibers can be compacted to form a sheet-like body that can be handled more readily. Two patents describe methods for producing compacted confections from spun sugar, namely Warning et al. U.S. Pat. No. 3,930,043 and Oiso et al. U.S. Pat. No. 4,526,525.

In U.S. Pat. No. 4,496,592 of Kuwahara et al. a chewing gum is described that is produced in the form of composite fibers by fiberizing a sugar and/or a candy and a chewing gum base or composition through a fiberizing section, such as a rotating cylinder, of a candy floss making machine.

Of the foregoing patents, none considers or suggests the possibility of using any form of fibrous sugar or cotton candy as a cosmetic or as a carrier for a cosmetic component.

With that as background, it has been discovered that many ingredients having cosmetic activity can be combined with a spinnable readily dissoluble material, such as sugar, in such manner that the resultant composition can still be spun into fiber form by melt spinning and without deteriorating the cosmetic material or reducing its effectiveness. Generally speaking, the particular sugar or other material used as a carrier agent should have a melting point that is a safe distance below that temperature at which the cosmetic ingredient might decompose or otherwise break down but not necessarily below the melting point of the cosmetic ingredient. Subject to that requirement, any material, such as sugar or a sugar-like substance that can be melt spun to produce a fibrous structure which substance dissolves rapidly in water, is non-toxic, and is compatible with the particular cosmetic, is suitable in the practice of the present invention.

From a dosage standpoint, it has also been discovered that the method to be described is able to produce with acceptable reliability consistent and uniform distribution of the cosmetic throughout the carrier agent. This is essential for cosmetic use where the quantity of effective material should be known or ascertainable.

The common sugar used for candy production is sucrose, and cotton candy made from sucrose is the product with which most people are familiar. But sucrose is not very stable in fiber form when exposed to moisture, even the slight moisture encountered in the atmosphere under normal atmospheric conditions. In addition, sucrose tends to be a sticky sugar. However, it has been discovered that other sugars such as lactose and maltose are much more stable and are not sticky. Additionally, it has been discovered that lactose and maltose in spun fibrous form have efficacy both as a hair conditioner, they seem to soften the hair, and as a skin softener.

The spinning process for producing "cotton candy" is a melt extrusion process in which the stock material is melted and forced through spinnerets. The conventional equipment uses a rotating spinning head surrounded by a bowl into which the fibers are spun. Using a cosmetic-sugar formulation, fibers are obtained. In order to convert the cotton-like mass to a form that can be packaged and handled, the as-spun product generally must be compacted to produce a compact body being careful not to squeeze too much. It is important that the final form retains its fibrous character so that it will dissolve rapidly when exposed to water or other solvent. At present, it is believed desirable for "tablet" production to reduce the initial spun volume by approximately two thirds or until the threshold is reached beyond which the fibers would fracture or coalesce. Preferably, the material is compacted as much as possible to produce a wafer-like structure while avoiding fracturing of the fibers or loss of the discrete fibrous identity. However, it will become apparent from the ensuing description that there will be occasions when a lesser degree of compaction or even no compaction is desirable.

Various procedures can be followed to produced discrete units where a discrete unit is desired. It is assumed that the cosmetic is uniformly distributed on or incorporated in the fibrous mass. A measured weight or volume of the as-spun product can be compacted as discrete units and sealed within a moisture proof package or wrapper. Alternatively, the as-spun product can be compacted on a continuous basis to produce a sheet or web which is subsequently subdivided to produce the individual units. These units can be packaged, preferably individually, using any known and appropriate technique that will exclude moisture since, depending upon the sugar, the fiber products have varying degrees of stability under normal humidity conditions.

Compaction of the fibrous mass can be accomplished before or during packaging or both. Partial compaction can be achieved between rollers or the like, with the resultant fibrous web entering between layers of packaging film. Then platens or the like can be applied to seal the individual units with squeezing of the film layers further compacting the fibers. The units can be severed either before, after or during the sealing step. Ultrasonic devices can be used to accomplish sealing and severing, or die cutters can be employed. It is contemplated that any suitable packaging technology can be employed so long as the packaging material excludes moisture and does not compress the fibrous mass to the point of destroying its fibrous structure.

At present, it is preferred to use a foil laminate material and allow the fiber product to cool to ambient temperature under controlled dry conditions before encapsulating in a foil laminate pouch. It has been found that attempts to seal the fiber product while still warm were unsatisfactory because of the tendency for moisture in the atmosphere to condense on the cool foil and remain trapped within the pouch to cause deterioration of the fiber structure. An acceptable packaging laminate is a mylar-foil laminate.

Any material capable of being spun into fibers and readily dissoluble in water may be used as the carrier agent. Presently preferred materials are sugars such as sucrose, maltose fructose, mannitol, sorbitol, glucose, lactose and xylotol. Particularly preferred, for example, is pure lactose. Lactose is a preferred sugar by reason of its relative stability under humid conditions. It is not sticky when moistened and is easier to handle. Also, it appears to have unique conditioning powers tending to act as an active antidesiccant and humectant, absorbing moisture from the air which is then either transferred to the hair or skin to maintain the moisture content of the latter or it prevents the hair or skin from drying out.

Additives, such as coloring agents, acceptable for external use, and which are compatible with the carrier agent and cosmetic ingredient, can be included in the product that is melt extruded.

The compounds discussed herein can be produced by coating the granules of the carrier agent with the cosmetic. In addition, the cosmetic ingredient can be distributed within the carrier by co-crystallization from a solution containing both the carrier agent and the cosmetic, or by any other known technique.

By way of more detailed explanation, a series of preparations for conditioning hair were prepared using a mucopolysaccharide, and later certain disaccharides.

EXAMPLE I

A mixture of 5% mucopolysaccharide and 95% mannitol w/w was prepared. The resulting mixture was spun using commercial cotton candy apparatus.

EXAMPLE II

A mixture of 5% mucopolysaccharide, 90% mannitol and 5% sucrose w/w was prepared and melted in an oven at 250° F. (121.1° C.), followed by cooling to solidify. The resulting solid solution was ground to a suitable particle size and spun using the apparatus of Example I.

EXAMPLE III

An aqueous solution of 5% mucopolysaccharide and 95% mannitol w/w was prepared and the resulting solution precipitated using a suitable solvent. The resulting precipitate was filtered and dried in an oven at a temperature less than 200° F. This yielded a uniform distribution of mucopolysaccharide and mannitol. The dried solid was ground to a suitable particle size and spun as in Examples I and II.

All three examples produced a fluff capable of being packaged as desired. The resultant fluff was intended for use on dampened freshly washed hair. For each example a suitable quantity was applied and rubbed onto the hair of a volunteer. The moisture in the hair served as a solvent for rapidly dissolving the fluff into solution. The hair was then dried and styled. The resulting hair appeared to be thicker and to have more body than before the application.

EXAMPLE IV

A granulated mixture of lactose (50 gm) and 2% mucopolysaccharide (1 gm) was prepared using isopropanol. The mixture was allowed to dry and then spun using a Gold Medal Company cotton candy machine that had been modified by fitting a plastic cover over the bowl. The cover caused the formation of a mushroom shaped dense fiber mass which flattened out when the spinner head was turned off. The fiber mass was dry due to the low relative humidity created inside the bowl as a result of the elevation in temperature resulting from heat trapped by the plastic cover. Unfortunately, lactose with a melting point above 200° C. requires a heat setting of the cotton candy apparatus to produce fibers which setting resulted in charring of the mucopolysaccharide that was used. This was attributed to the presence of animal protein matter.

EXAMPLE V

Plain lactose was spun with the Gold Medal Company cotton candy apparatus at the highest heat setting producing excellent fluff. Portions of the fluff were taken and sprinkled with dry mucopolysaccharide in powder form. The lactose fiber fluff was folded over to envelope the mucopolysaccharide. Three samples were prepared, with 3%, 6% and 10% mucopolysaccharide, respectively, based upon an aliquot of 0.5 gm lactose. In user tests it was felt that 0.5 gm was too large a quantity.

EXAMPLE VI

Plain lactose was spun as in example V and, without the addition of mucopolysaccharide, aliquot portions were packaged in polyester pouches. Subsequently, the plain lactose was applied to wet hair with excellent results. It added thickness and body to the hair and eliminated the need for a setting lotion.

It is apparent that additional active agents can be added such as biotin for scalp enrichment and nicotinamide compounds to stimulate blood flow in the capillaries of the scalp. Also, fragrances can be added if desired.

From user reaction it has been determined that about 0.1–0.2 grams of lactose is optimum. This quantity has a fiber mass approximately ½ inch in diameter and ⅛ inch thick. It was found sufficient to give body to the hair without leaving an undesirable stiffness.

Preservatives in the dry lactose are not necessary. However, if a diluent is provided various preservatives can be used such as methyl and propyl paraben, sodium bisulfite, SD-40 alcohol, and the like.

The above examples involve applying dry fibrous material directly to wet air. However, spun lactose can be used differently. In its bulk spun uncompressed state, lactose was mixed with ordinary tap water in a container in the ratio of 4 to 5 parts to one part lactose. The solution was then applied to the hair after shampooing and the hair was blow dried with excellent results. Surprisingly, this treatment after a few hours seemed to provide softer hair, unlike alcohol based products that have the reverse effect.

In another test, the solution prepared by dissolving one part lactose in 4 to 5 parts water, was rubbed on the skin of a tester. The skin became smooth and seemed to increase in smoothness as time passed. It is theorized that the spun lactose is functioning as an active antidesiccant and humectant extracting moisture from the atmosphere and then either imparting the moisture to the skin or preventing the skin from drying out to thereby maintain skin softness.

Various considerations enter into the choice of sugar, or sugars for use as the carrier for a given cosmetic. As mentioned previously, the spin temperature must not exceed the deterioration temperature for the specific active agent. Table I lists the melting points of various sugars, all of which can be spun into fibers.

TABLE I

| SUGAR | | MELTING POINT | |
|---|---|---|---|
| | | °C. | °F. |
| maltose | R | 103 | 217.4 |
| fructose | USP | 105 | 221.0 |
| sorbitol | USP | 110 | 230.0 |
| dextrose | USP | 146 | 294.8 |

TABLE I-continued

| SUGAR | | MELTING POINT | |
|---|---|---|---|
| | | °C. | °F. |
| xylose | R | 153 | 307.4 |
| mannitol | USP | 166 | 330.8 |
| sucrose | USP | 186 | 366.8 |
| lactose | R | 202 | 395.6 |

As a result of storage tests it has been discovered that sucrose is extremely susceptible to deterioration in the presence of moisture. However, it has been discovered that combining as little as 10% lactose with the sucrose produces a fibrous product after spinning that is significantly more stable. The lactose has the physical ability of absorbing moisture without crumbling and, as previously mentioned, functions as an active antidesiccant. The lactose over time merely becomes softer and smoother. This becomes evident when pure lactose is spun and observed. Of course, pure lactose is an excellent carrier agent.

Of the various sugars, maltose and lactose when spun into fibers are much more stable than sucrose, that is, they are less affected by humidity. Consequently, it is presently preferred to include at least a small quantity of either lactose or maltose in any sugar carrier.

Experience to date has shown that sucrose and lactose can be spun with excellent results. Maltose because of its low melting point is ideal for certain cosmetics. However, it has been discovered that when maltose is spun using present equipment that is capable of rotating its spinneret at 4000 R.P.M., the resultant fibers are much shorter than those obtained with sucrose or lactose. It is believed, however, that longer fibers of maltose can be obtained by using higher spinneret speed.

Attempts to spin methyl cellulose with present equipment at 4000 R.P.M. have been met with gumming and charring of the material. It is believed that this problem also will be overcome by using higher spinneret speed and/or adjusting the size of the grid opening.

Because of the rapid release of a cosmetic when in fiber form and exposed to moisture, the instant product form is ideally suited for use in topical delivery of a cosmetic.

Numerous examples have been mentioned above. However, the fundamental concept of transforming a cosmetic into fiber form, wherein a fiber producing material acts somewhat as a scaffold to support the cosmetic for entry into solution almost instantaneously, can be applied to an extensive array of materials. In table II below, the examples of useful categories are set forth having cosmetological application.

TABLE II

| COSMETIC CATEGORY |
|---|
| ACNE PREPARATIONS |
| ANTIFUNGAL |
| ANTITRICHOMONAL |
| ANTIVIRAL AGENTS |
| ANTIPRURITICS |
| SUN SCREEN |
| BURN AGENTS |
| ANESTHETIC AGENTS |

It should be understood that under certain circumstances a transdermal systemic medicament can be added to the otherwise topical cosmetic without interfering with the cosmetic action.

A useful method of packaging and using the present invention will be explained with reference to a typical sun screen. Using Para-Aminobenzoic Acid (PABA), it can be spun with a suitable sugar to produce a mass of fibrous material which, in a controlled quantity, is placed in a vial or capsule of predetermined internal volume larger than the volume of the fibrous cosmetic mass. The vial or capsule can be sealed in any suitable manner until use is desired. At time of use the vial or capsule is opened and water is added, either to a fill mark or until the container is filled, and the resulting solution is applied to the skin as a sun screen. The fibrous mass goes into solution almost instantaneously and leaves no residue.

Having described the present invention with reference to the presently preferred embodiments thereof, it will be apparent to those skilled in the subject art that various changes and modifications can be incorporated without departing from the true spirit of the invention as defined in the appended claims.

What is claimed is:

1. A spun fibrous cosmetic composition comprising a rapidly dissoluble mass of water soluble spun fibers of a material capable of being spun into fibers that are readily water-soluble, and an effective quantity of an active agent distributed on or incorporated in said fibrous mass where said active agent has cosmetologic activity.

2. A spun fibrous cosmetic composition according to claim 1, wherein said active agent is a mucopolysaccharide.

3. A spun fibrous cosmetic composition according to claim 2, wherein there is about 3% to 10% by weight of mucopolysaccharide in said composition.

4. A spun fibrous cosmetic composition according to claim 3, wherein said material is mannitol and represents about 95% by weight of said composition, with about 5% by weight of mucopolysaccharide.

5. A spun fibrous cosmetic composition according to claim 3, wherein said material comprises about 90% by weight of mannitol and about 5% by weight of sucrose, with about 5% mucopolysaccharide.

6. A spun fibrous cosmetic composition according to claim 3, wherein said active agent includes a constituent selected from the group consisting of biotin, nicotinamide compounds, and combinations thereof.

7. A spun fibrous cosmetic composition according to claim 1, wherein said active agent is a sun screen.

8. A spun fibrous cosmetic composition according to claim 1, wherein said active agent is a hair conditioner.

9. A spun fibrous cosmetic preparation comprising a rapidly dissoluble mass of water soluble spun fibers of lactose.

10. A spun fibrous cosmetic preparation according to claim 9, wherein a sun screen material is distributed on or incorporated in said mass of fibers.

11. A spun fibrous cosmetic preparation according to claim 10, wherein said sun screen comprises Para-Aminobenzoic Acid.

12. A spun fibrous cosmetic preparation according to claim 9, wherein between about 3% and 10% mucopolysaccharide by weight is distributed on or incorporated in said mass of fibers.

13. A spun fibrous cosmetic preparation according to claim 12, wherein a constituent selected from the group consisting of biotin, nicotinamide compounds, and combinations thereof is distributed on or incorporated in said mass of fibers.

14. A spun fibrous cosmetic preparation according to claim 9, wherein a constituent selected from the group consisting of biotin, nicotinamide compounds, and combinations thereof is distributed on or incorporated in said mass of fibers.

15. A method for treating hair or skin cosmetically which comprises applying to hair or skin a spun fibrous cosmetic preparation comprising a rapidly dissoluble mass of water soluble spun fibers of lactose.

16. A method according to claim 15, which comprises applying water to the hair or skin to wet the same before applying said cosmetic preparation thereto.

17. A method according to claim 15, which comprises dissolving said mass of spun fibers in water and applying the resultant solution to said hair or skin.

18. A method for treating hair or skin cosmetically which comprises applying to hair or skin a spun fibrous cosmetic composition comprising a rapidly dissoluble mass of water soluble spun fibers of a material capable of being spun into fibers that are readily water-soluble, and an effective quantity of an active agent distributed on or incorporated in said fibrous mass where at least said active agent has cosmetologic activity.

19. A method according to claim 18, wherein said active agent is a mucopolysaccharide.

20. A method according to claim 18, wherein said active agent is a sun screen.

21. A method according to claim 18, wherein said active agent is a hair conditioner.

22. A method according to claim 18, wherein said mass of spun fibers comprise lactose fibers.

23. A method according to claim 22, wherein said active agent is a mucopolysaccharide.

24. A method according to claim 22, wherein said active agent is a sun screen.

25. A method according to claim 22, wherein said active agent is a hair conditioner.

* * * * *